United States Patent
Kim et al.

(10) Patent No.: US 6,773,159 B2
(45) Date of Patent: Aug. 10, 2004

(54) NON-INVASIVE APPARATUS FOR MEASURING A TEMPERATURE OF A LIVING BODY AND METHOD THEREFOR

(75) Inventors: Tae-woo Kim, Seongnam (KR); Sang-min Lee, Seoul (KR); Jeong-whan Lee, Suwon (KR); Sang-jin Eom, Incheon (KR); Wan-taek Han, Suwon (KR)

(73) Assignee: Samsung Electronics Co., Ltd., Kyungki-do (KR)

( * ) Notice: Subject to any disclaimer, the term of this patent is extended or adjusted under 35 U.S.C. 154(b) by 0 days.

(21) Appl. No.: 10/390,017

(22) Filed: Mar. 18, 2003

(65) Prior Publication Data

US 2003/0179808 A1 Sep. 25, 2003

(30) Foreign Application Priority Data

Mar. 21, 2002 (KR) ........................................ 2002-15371

(51) Int. Cl.[7] .............................. A61B 5/00; A61B 5/05; G01J 5/00
(52) U.S. Cl. .......................... 374/122; 374/101; 374/43; 374/44; 374/45; 600/549; 600/407
(58) Field of Search ............................. 374/122, 44–45, 374/101, 1, 43, 121; 600/407, 547, 549; 324/315, 303; 327/512; 340/870.1

(56) References Cited

U.S. PATENT DOCUMENTS

| | | | |
|---|---|---|---|
| 4,301,412 A | * 11/1981 | Hill et al. ..................... | 324/442 |
| 5,068,619 A | * 11/1991 | Nakano et al. ............. | 324/715 |
| 5,149,198 A |   9/1992 | Sterzer ........................ | 374/139 |
| 5,293,877 A | *  3/1994 | O'Hara et al. .............. | 600/549 |
| 5,435,646 A | *  7/1995 | McArthur et al. .......... | 374/185 |
| 5,673,692 A | * 10/1997 | Schulze et al. ............. | 600/301 |
| 5,688,050 A |  11/1997 | Sterzer et al. .............. | 374/122 |
| 5,841,288 A | * 11/1998 | Meaney et al. ............. | 324/639 |
| 5,897,505 A | *  4/1999 | Feinberg et al. ............ | 600/547 |
| 5,949,845 A |   9/1999 | Sterzer ........................ | 378/37 |
| 6,023,637 A | *  2/2000 | Liu et al. ..................... | 600/474 |
| 6,132,083 A | * 10/2000 | Enala ........................... | 374/44 |
| 6,167,258 A | * 12/2000 | Schmidt et al. ............. | 455/419 |
| 6,221,025 B1 | *  4/2001 | Skoletsky ................... | 600/504 |
| 6,236,886 B1 | *  5/2001 | Cherepenin et al. ........ | 600/547 |
| 6,273,904 B1 | *  8/2001 | Chen et al. .................. | 607/88 |
| 6,292,682 B1 | *  9/2001 | Kruger ........................ | 600/407 |
| 6,332,087 B1 | * 12/2001 | Svenson et al. ............. | 600/407 |
| 6,375,624 B1 | *  4/2002 | Uber et al. .................. | 600/549 |
| 6,491,425 B1 | * 12/2002 | Hammiche et al. ........... | 374/43 |
| 6,543,933 B2 | *  4/2003 | Stergiopoulos et al. ..... | 374/122 |
| 6,567,688 B1 | *  5/2003 | Wang .......................... | 600/430 |
| 6,595,929 B2 | *  7/2003 | Stivoric et al. ............. | 600/549 |
| 2002/0103425 A1 | *  8/2002 | Mault .......................... | 600/373 |
| 2002/0156358 A1 | * 10/2002 | Lee et al. .................... | 600/407 |

OTHER PUBLICATIONS

F. Sterzer Automedica, 1987, vol. 8, pp. 203–211, "Microwave Radiometers for Non–invasive Media" Radio Science.
F. Bardati et al, 1983, vol. 18, pp. 1393–1401, "Radiometric sensing of Biological Layered Media", Radio Science.

\* cited by examiner

Primary Examiner—Gail Verbitsky
(74) Attorney, Agent, or Firm—Lee & Sterba, P.C.

(57) ABSTRACT

A non-invasive apparatus and method for measuring a temperature of a portion of a living body, includes a signal receiving unit receiving electromagnetic wave signals emitted from the portion of a living body to be measured, a signal processing unit processing the electromagnetic signals input from the signal receiving unit and outputting a radiation power signal, a medium characteristic measurement unit measuring a value of a conductivity or a permittivity of the portion of the living body to be measured and outputting the measured value, and a temperature conversion unit including a computer database storing a plurality of temperature conversion tables with respect to radiation power according to the conductivity or the permittivity of the portion of the living body and determining a corresponding temperature using the measured value of the conductivity or the permittivity of the portion of the living body and the radiation power signal of the signal processing unit.

13 Claims, 10 Drawing Sheets

NON-INVASIVE APPARATUS FOR MEASURING A TEMPERATURE OF A LIVING BODY AND METHOD THEREFOR

BACKGROUND OF THE INVENTION

1. Field of the Invention

The present invention relates to an apparatus and a method for measuring a temperature of a living body. More particularly, the present invention relates to a non-invasive apparatus for measuring an internal temperature of a living body by measuring the electromagnetic wave characteristics of a medium, and a method therefor.

2. Description of the Related Art

In order to detect and treat an abnormal state of a human body, a non-invasive apparatus and a method for measuring a temperature of a living body by measuring microwaves emitted from the living body have been developed. When the temperature of a medium is greater than absolute zero, electromagnetic waves are emitted according to a principle of black body radiation. If the medium is a living body, electromagnetic wave signals are emitted from the inside of the living body to the outside of the skin of the living body. The temperature of abnormal tissues, which is higher than the temperature of normal tissues, can be detected by measuring the electromagnetic waves emitted from a predetermined portion of the living body and converting the measured electromagnetic waves into a temperature, so that an abnormal state of the living body may be detected at an early stage.

FIG. 1 is a functional diagram of a conventional apparatus employing a microwave radiometer to measure the temperature of a specimen according to the prior art.

Referring to FIG. 1, a specimen 100 emits electromagnetic radiation 102 having a certain intensity and frequency-spectrum distribution, each of which is a function of the temperature of the specimen 100 and the characteristics of the material the specimen 100 is composed of. The frequency-spectrum distribution includes a portion of a microwave interval to which a microwave antenna unit 104 is responsive. The temperature of the specimen 100 is sensed by the microwave antenna unit 104, which is positioned in a cooperative spatial relationship with the specimen 100 to receive part of electromagnetic radiation 102, which is within this microwave interval.

A microwave radiometer 105, including a microwave receiver 106, a reference microwave noise source 108, and a temperature meter 110, compares the relative intensity of the microwave noise output from the microwave antenna unit 104 with respect to the intensity of the output from the reference microwave noise source 108. The temperature of the specimen 100 is indicated by the temperature meter 110 in response to the output from the microwave receiver 106 applied as an input thereto.

The conventional apparatus for measuring a temperature of a living body stores a temperature conversion table, established from a temperature conversion graph, with respect to a specific medium as shown in FIG. 2. The conventional apparatus determines temperatures according to the measured emitted intensities.

Referring to FIG. 2, the emitted intensity and the temperature are in a linearly proportional relationship. In other words, as the emitted intensity increases, the detected temperature increases linearly. Thus, a specific temperature corresponding to a specific emitted intensity can be selected. However, the graph of FIG. 2 may be applied only to a predetermined portion of a living body having a specific permittivity or conductivity. If the permittivity or the conductivity is changed within the living body, it is preferable to use an alternate graph.

As shown in FIG. 3, radiation power, i.e., received electric power, emitted at the same temperature may vary when the permittivity or the conductivity is different so that errors occur in the conversion process of a measured emitted intensity into a temperature by using a single temperature conversion table.

For example, if a received electric power measured at a predetermined portion of a living body having a permittivity of 49.8 is $4 \times 10^{-16}$ W, a converted temperature according to the graph f1 is 46.5° C. However, a converted temperature for the same electric power according to the graph f2, which represents a predetermined portion of a living body having a permittivity of 9.8, is 38° C., so that a difference of 8.5° C. occurs.

For example, in a case where the temperature of breasts that have large deviations of the permittivity and the conductivity from 9.8 to 51.3 S/m and 0.37 to 3.4 S/m, respectively, is measured, the deviation of emitted intensity due to the differences of the permittivity and the conductivity cannot be corrected using a single temperature conversion table. Accordingly, a large deviation occurs in the converted temperature. As a result, abnormal tissues may be determined as normal tissues thereby preventing the detection of an abnormal state in a living body.

SUMMARY OF THE INVENTION

In an effort to solve the above and related problems, it is a feature of an embodiment of the present invention to provide an apparatus and a method for measuring an internal temperature of a living body with improved reliability.

To provide this feature of an embodiment of the present invention, an apparatus for measuring a temperature of a portion of a living body includes a signal receiving unit for receiving electromagnetic wave signals emitted from the portion of a living body to be measured, a signal processing unit for processing the electromagnetic signals input from the signal receiving unit and outputting a radiation power signal, a medium characteristic measurement unit for measuring a value of a conductivity or a permittivity of the portion of the living body to be measured and for outputting the measured value, and a temperature conversion unit, including a computer database for storing a plurality of temperature conversion tables with respect to radiation power according to the conductivity or the permittivity of the portion of the living body, for determining a corresponding temperature using the measured value of the conductivity or the permittivity of the portion of the living body and the radiation power signal of the signal processing unit.

The signal receiving unit preferably includes a receiver for receiving the electromagnetic signals and a transmission line for sending the electromagnetic wave signals from the receiver to the signal processing unit. It is also preferable that the receiver is an antenna or a probe.

The signal processing unit preferably includes an amplifier for amplifying the electromagnetic wave signals input from the signal receiving unit, a filter for extracting a signal value of a predetermined frequency band from the electromagnetic wave signals, a noise source for maintaining a reference signal of a specific temperature, a switch for switching the extracted signal and the reference signal within a specific interval and for connecting to a next stage, an isolator for processing the extracted signal in one direction and matching circuits, and a detector for detecting an enveloped curve of the extracted signal.

The temperature conversion unit preferably includes an information storage unit having a computer database for storing the plurality of temperature conversion tables with respect to radiation power, and an information processing unit for selecting a proper temperature conversion table corresponding to the conductivity or the permittivity measured by the information storage unit and for determining the temperature corresponding to the radiation power signal of the electromagnetic wave input from the signal processing unit, from the temperature conversion tables.

The medium characteristic measurement unit preferably includes a signal generator for generating an electromagnetic wave signal of a specific frequency band, a transmitter for sending the electromagnetic wave signal to the portion of the living body, a receiver for receiving the electromagnetic wave signal passed through the portion of the living body to be measured, a signal processor for receiving the electromagnetic wave signal from the receiver and processing the received signal, and a controller for controlling the signal generator and the signal processor.

The receiver preferably receives the electromagnetic wave signal reflected on the portion of the living body to be measured.

It is preferable that the apparatus further includes a display for displaying the temperature selected by the temperature conversion unit.

To provide another feature of an embodiment of the present invention, a method for measuring a temperature of a portion of a living body includes receiving electromagnetic wave signals from the portion of a living body to be measured, processing the received electromagnetic wave signals and extracting a radiation power signal therefrom, measuring medium characteristics, such as a conductivity or a permittivity, of the portion of the living body to be measured, and converting a temperature for determining the temperature of the portion of the living body based on the radiation power signal of the received electromagnetic wave signals and the conductivity or the permittivity of the measuring medium characteristics process.

Processing the received electromagnetic signals preferably includes removing noise from the electromagnetic wave signals, extracting the electromagnetic wave signal of a specific frequency band, and amplifying the extracted signal value.

Measuring medium characteristics preferably includes radiating the electromagnetic wave signal of a specific frequency band to the portion of the living body to be measured, receiving the electromagnetic wave signal passed through the portion of the living body to be measured, and calculating a conductivity or a permittivity based on the received electromagnetic wave signal.

Converting a temperature preferably includes selecting a specific temperature conversion table corresponding to the conductivity or the permittivity from a plurality of temperature conversion tables with respect to radiation power, which are previously stored, and calculating a specific temperature corresponding to the radiation power of the electromagnetic wave from the temperature conversion table.

In operation, the present invention stores a temperature conversion table corresponding to a permittivity or a conductivity in a radiometer as a computer database, and measures the permittivity or the conductivity of a medium. Thereafter, the measured electromagnetic wave is converted into a temperature with reference to the temperature conversion table corresponding to the measured constant. Therefore, when measuring the internal temperature of a living body, reliability of the measured temperature is improved.

BRIEF DESCRIPTION OF THE DRAWINGS

The above and other features and advantages of the present invention will become more apparent to those of ordinary skill in the art by describing in detail preferred embodiments thereof with reference to the attached drawings in which.

DETAILED DESCRIPTION OF THE INVENTION

Figure 1:
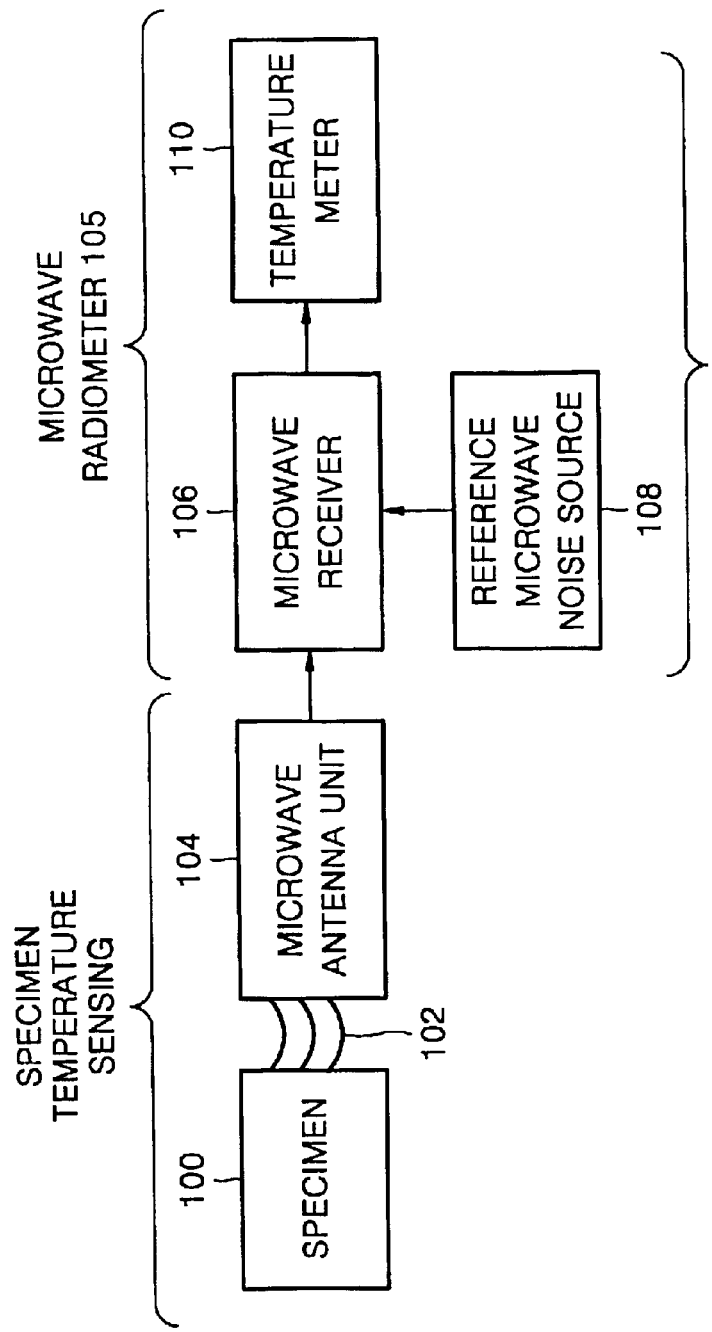
FIG. 1 is a functional diagram of a conventional apparatus employing a microwave radiometer to measure the temperature of a specimen according to the prior art.
Figure 2:
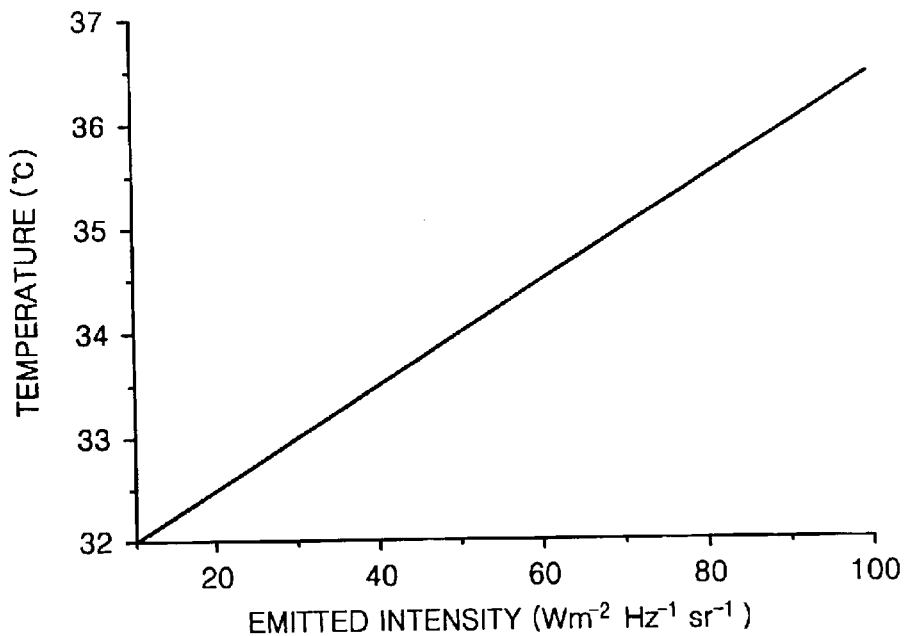
FIG. 2 is a graph illustrating a conventional living body temperature conversion table.
Figure 3:
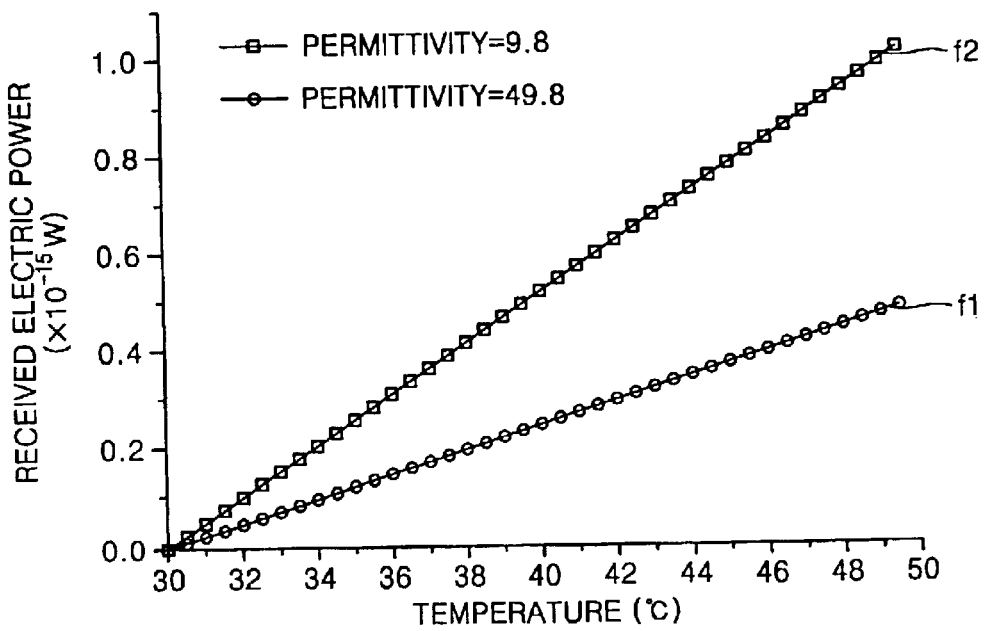
FIG. 3 is a graph illustrating changes in an emitted energy of a living body according to changes in a temperature with respect to a permittivity and a conductivity of a living body medium.

Korean Patent Application No. 2002-15371, filed Mar. 21, 2002, and entitled: "Non-Invasive Measuring Apparatus of Living Body Temperature and Method Therefor," is incorporated by reference herein in its entirety.

The present invention will now be described more fully with reference to the accompanying drawings, in which preferred embodiments of the invention are shown. Like reference numerals refer to like elements throughout.

Figure 4:
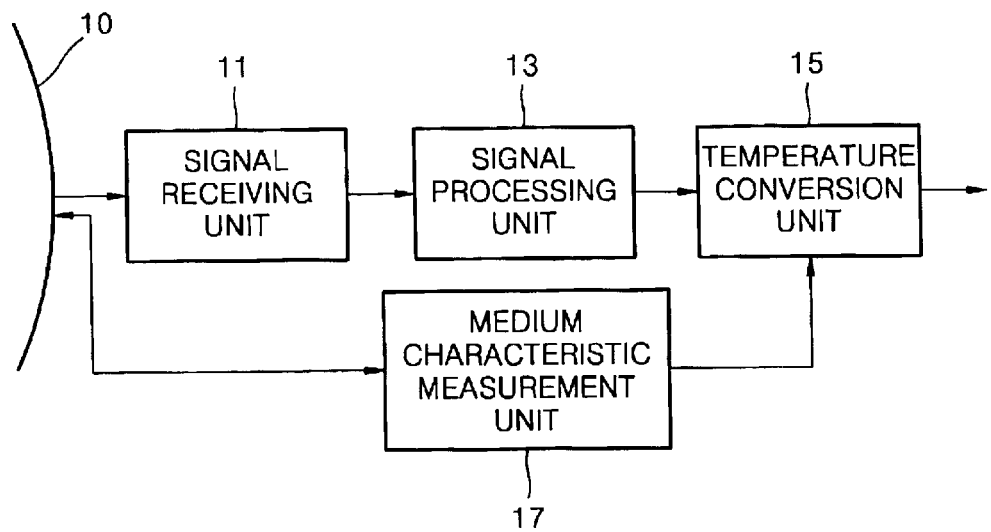
FIG. 4 is a block diagram illustrating an apparatus for measuring a living body temperature according to an embodiment of the present invention.

FIG. 4 is a block diagram illustrating a non-invasive apparatus for measuring a temperature of a living body according to an embodiment of the present invention.

Referring to FIG. 4, the non-invasive apparatus for measuring a temperature of a living body includes a signal receiving unit 11 and a signal processing unit 13. The signal receiving unit 11 receives electromagnetic wave signals emitted from a portion of a human body 10 to be measured. The signal processing unit 13 switches the electromagnetic wave signals of the signal receiving unit 11 with a reference signal of a noise source to pass an isolator in order to match circuits, filters the electromagnetic wave signal of a specific frequency band to pass the electromagnetic wave signal, amplifies the filtered signal, and detects an enveloping curve.

In addition, the non-invasive apparatus for measuring a living body temperature further includes a medium characteristic measurement unit 17 and a temperature conversion unit 15. The medium characteristic measurement unit 17 measures the conductivity or the permittivity of the portion of the living body 10 to be measured and sends the measured value to the temperature conversion unit 15. The temperature conversion unit 15 includes a computer database having a plurality of temperature conversion tables with respect to radiation power. In addition, the temperature conversion unit 15 selects a temperature conversion table corresponding to the measured conductivity or permittivity, and selects the temperature corresponding to the radiation power of the electromagnetic wave input from the signal processing unit 13, from the temperature conversion table.

The signal receiving unit 11 receives the electromagnetic waves of a specific frequency band emitted from the portion of a living body, such as a human body 10. The signal receiving unit 11 includes an antenna (21 of FIG. 5) for receiving electromagnetic wave signals, a receiver having a probe or a transmission line, and a transmission line for sending the electromagnetic wave signals from the receiver to the signal processing unit 13.

Figure 5:
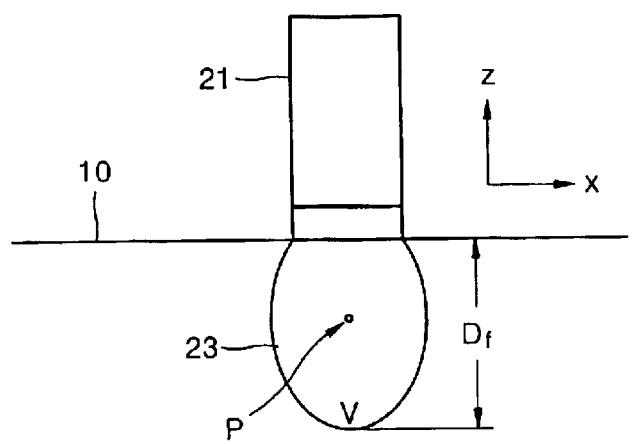
FIG. 5 illustrates a schematic view of an antenna emission pattern with respect to a living body tissue.

The antenna 21 included in the signal receiving unit 11 is illustrated in FIG. 5. The antenna 21 contacts the human body 10 to receive the electromagnetic waves emitted from the portion of the human body 10 to be measured.

Referring to FIG. 5, the antenna 21 aligned in a direction of the Z-axis receives the electromagnetic wave signals emitted from a point p of the human body 10 and sends the received electromagnetic wave signals to the signal processing unit 13 via the transmission line. The electromagnetic wave emitted from the point p penetrates to a skin depth $D_f$ while forming an oval shape 23. Such electromagnetic waves emitted from a specific portion of the human body 10 have different penetration depths into the skin according to the conductivity and the permittivity of the specific portion, which will be described with reference to FIG. 9.

The electromagnetic wave signals received by the antenna 21 are sent to the signal processing unit 13 through the transmission line. The signal processing unit 13 includes an amplifier for amplifying the electromagnetic wave signals input from the signal receiving unit 11, a filter for extracting signal values of a predetermined frequency band from the electromagnetic wave signals, a noise source for maintaining a reference signal with respect to a predetermined temperature, a switch for switching the extracted signal and the reference signal with a predetermined interval and for connecting to a next stage, an isolator for processing the extracted signal in one direction and maintaining the matched state of circuits, and a detector for detecting the enveloped curve of the extracted signal, in order to easily process signals in the temperature conversion unit 15.

Figure 6:
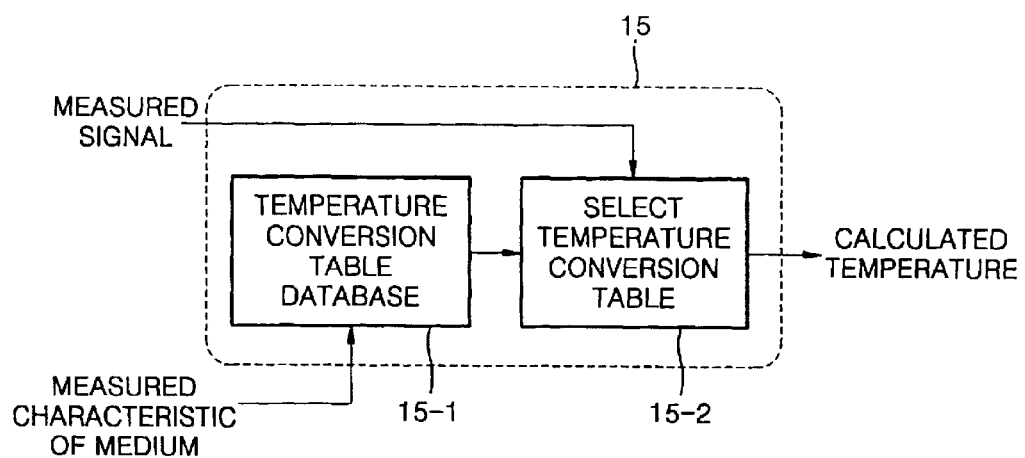
FIG. 6 is a block diagram illustrating a temperature conversion unit of an apparatus for measuring a temperature of a living body according to an embodiment of the present invention.

Referring to FIG. 6, the temperature conversion unit 15 selects a temperature conversion table 15-2 corresponding to the permittivity or the conductivity sent from the medium characteristic measurement unit 17, from temperature conversion tables 15-1 with reference to radiation power, which are previously stored. In addition, the temperature conversion unit 15 calculates the temperature corresponding to the radiation power of the measured signal sent from the signal processing unit using the selected temperature conversion table 15-2.

The temperature conversion unit 15 includes an information storage unit, such as a software having a computer database that stores the temperature conversion tables 15-1 with respect to radiation power, an information processing unit, such as a microcomputer, for selecting a specific temperature conversion table corresponding to the permittivity or the conductivity from the information storage unit and for calculating the temperature corresponding to the radiation power using the temperature conversion tables, and a display for displaying the calculated temperature.

Figure 7:
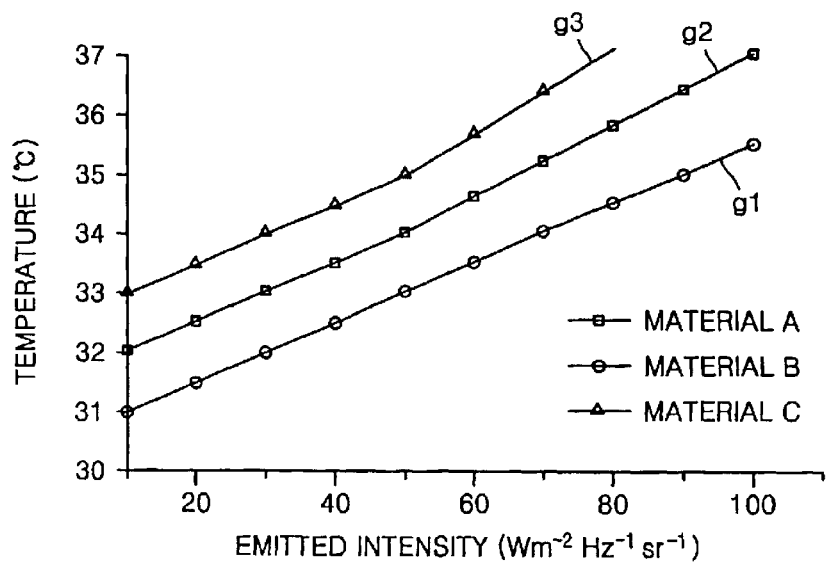
FIG. 7 is a graph illustrating a temperature conversion table of a temperature conversion unit in an apparatus for measuring a temperature of a living body according to an embodiment of the present invention.

FIG. 7 is an example of the computer database 15-1 storing the temperature conversion tables.

Referring to FIG. 7, changes in the temperature with respect to material A is represented as a graph g2, changes in the temperature with respect to material B is represented as a graph g1, and changes in the temperature with respect to material C is represented as a graph g3.

For example, if the emitted intensity of the material A is 50 $Wm^{-2} \cdot Hz^{-1} \cdot sr^{-1}$, the temperature of the material A is about 34° C. with reference to the graph g2, which is a temperature conversion table of material A. At the same emitted intensity, the temperature of the material B is about 33° C. with reference to the graph g1 and the temperature of the material C is about 35° C. with reference to the graph g3. If the graph g1 or g3, which is the temperature conversion table of material B or C, is applied to the electromagnetic wave signal from the material A, a temperature different from the actual temperature of the material A is selected.

In order to prevent such an error, the present invention includes the medium characteristic measurement unit 17 for measuring the medium characteristics of the portion to be measured and selecting the temperature conversion table according to the medium characteristics of the portion. This is because the information on the characteristics of the material is necessary to select the appropriate temperature conversion table from the temperature conversion tables of materials A, B, and C, as shown in FIG. 7.

The medium characteristic measurement unit 17 measures the medium characteristics, i.e., permittivity and conductivity, of the portion of the living body to be measured and sends the measured values to the temperature conversion unit 15. Each of FIGS. 8A and 8B illustrates a transmission-type medium characteristic measurement unit and a reflection-type medium characteristic measurement unit.

Figure 8A:
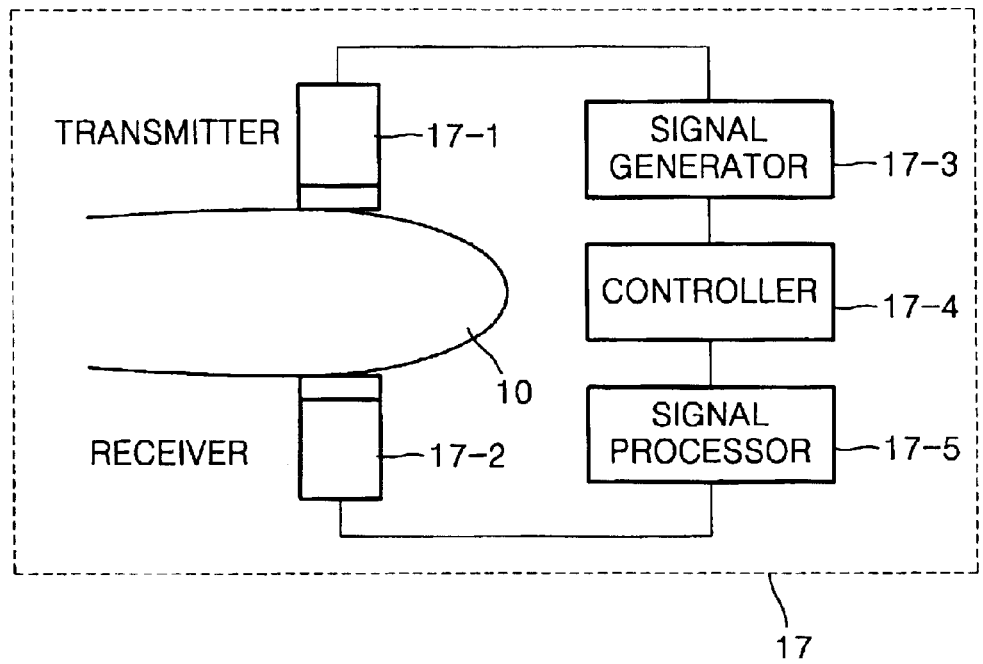
FIG. 8A illustrates a view of a transmission-type medium characteristic measurement unit in an apparatus for measuring a temperature of a living body according to an embodiment of the present invention.

Referring to FIG. 8A, a transmission-type medium characteristic measurement unit 17 includes a signal generator 17-3 for generating electromagnetic wave signals of a specific frequency band, a transmitter 17-1 for radiating the electromagnetic wave signals toward a predetermined portion of a human body, a receiver 17-2 for receiving the electromagnetic wave signals radiated from the transmitter 17-1 and transmitted human tissues 10, a signal processor 17-5 for processing the output value of the receiver 17-2, and a controller 17-4 for controlling the electromagnetic wave signals radiated from the signal generator 17-3 and the electromagnetic wave signals received by the signal processor 17-5. Here, the controller 17-4 further controls the amount and timing of the signals to be transmitted and received.

Figure 8B:
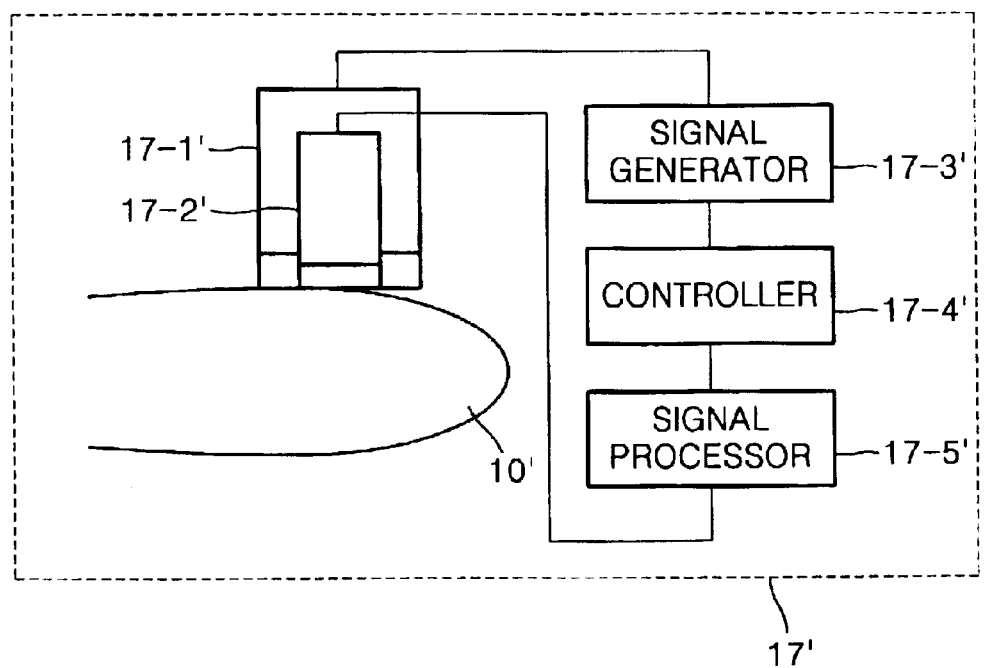
FIG. 8B illustrates a view of a reflection-type medium characteristic measurement unit in an apparatus for measuring a temperature of a living body according to an embodiment of the present invention.

A reflection-type medium characteristic measurement unit 17' of FIG. 8B includes elements similar to the transmission-type medium characteristic measurement unit 17, i.e., a signal generator 17-3', a transmitter 17-1', a receiver 17-2', a signal processor 17-5', and a controller 17-4'. In this case, however, the transmitter 17-1' and the receiver 17-2' are integrally formed to receive the electromagnetic wave signals reflected on a predetermined portion 10' of a human body.

If the permittivity and the conductivity measured in the medium characteristic measurement unit 17 are sent to the temperature conversion unit 15 while sending the electromagnetic wave signals of the signal receiving unit 11 to the temperature conversion unit 15 after processing the signals in the signal processing unit 13, the temperature conversion unit 15 selects the temperature conversion table corresponding to the measured permittivity and conductivity amount from the temperature conversion tables with respect to an electromagnetic wave amount that are previously stored. Thereafter, the temperature conversion unit 15 searches the temperature corresponding to the electromagnetic wave on the temperature conversion table.

The apparatus and method for measuring a temperature of a living body according to the present invention are based on the principle that radiation power varies according to the permittivity or the conductivity as described in Equation 1.

$$B_{fr} = B_f (e^{-az})^2$$

$$B_f = 2k_0 T/\lambda^2, \ (k_0 = 1.38 \times 10^{-23} J/K) \quad (1)$$

Here, $B_f$ represents the radiation amount of electromagnetic waves by the temperature based on the Planck's law and the Rayleigh-Jeans' law. In addition, T represents an absolute temperature in K degrees, $\lambda$ represents a wavelength m, and a represents an attenuation constant that is calculated by Equation 2.

$$a = k\left[\sqrt{1+\tan^2\delta} - 1\right)/2\right]^{1/2}, \ (\text{here, } \tan\delta = \sigma/\omega\varepsilon)$$

$$\lambda = \frac{1}{f\sqrt{\mu\varepsilon}} \quad (2)$$

Here, $\sigma$ represents a conductivity, $\varepsilon$ represents a permittivity, and $\omega = 2\pi f$. In addition, k represents a wave number.

In other words, since radiation power is dependent upon the conductivity or the permittivity, a precise radiation power can be detected by measuring the conductivity or the permittivity of a predetermined portion of a living body. In addition, the detected radiation power is a function of temperature according to Equation 1, so that temperature can be calculated according to radiation power.

Figure 9:
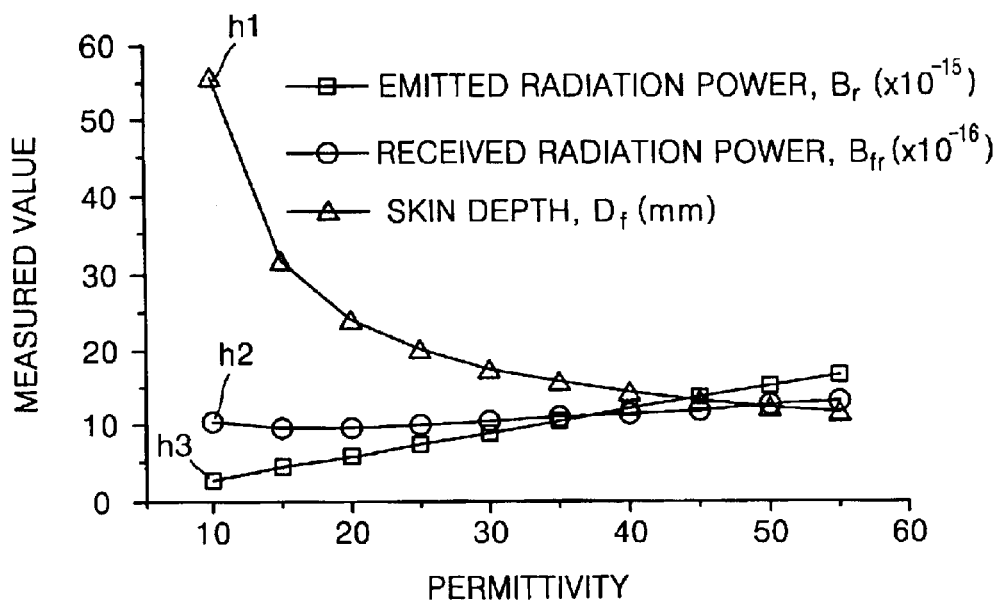
FIG. 9 is a graph illustrating changes in the emitted energy and penetration depth of a living body according to changes in a permittivity and a conductivity.

FIG. 9 is a graph illustrating changes in the emitted radiation power $B_f$, the received radiation power $B_{fr}$, and the penetration depth $D_f$ of a living body according to changes in the permittivity.

Referring to FIG. 5 and a graph h1 of FIG. 9, as the permittivity increases, the penetration depth $D_f$ of electromagnetic wave decreases. When the permittivity is 10, $D_f$ is about 55 mm. However, when the permittivity is 55, $D_f$ is reduced to about 10 mm.

Referring to a graph h3 of FIG. 9, the emitted radiation power $B_f$, about $2 \times 10^{-15}$ at a permittivity of 10, linearly increases to $15 \times 10^{-15}$ at a permittivity of 55. Referring to a graph h2 of FIG. 9, the received radiation power $B_{fr}$, according to the emitted radiation power maintain the level of about $10^{-15}$ when the permittivity varies from 10 to 60.

Figure 10:
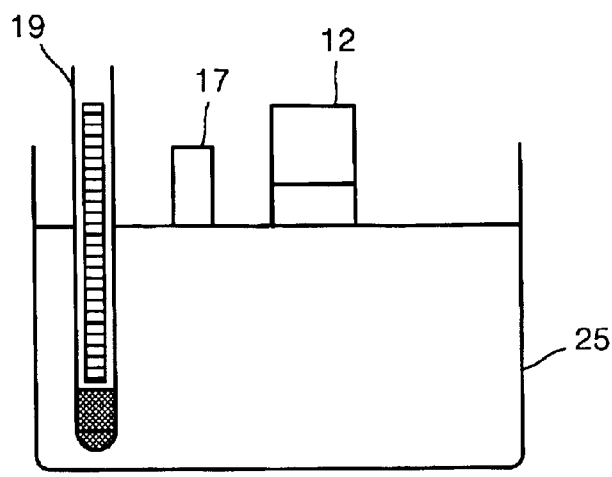
FIG. 10 illustrates a view of a device for establishing a temperature conversion table of an apparatus for measuring a temperature of a living body according to an embodiment of the present invention.

FIG. 10 illustrates a view of a device for establishing the temperature conversion tables of an apparatus for measuring a temperature of a living body according to an embodiment of the present invention.

Referring to FIG. 10, a medium, such as distilled water or a mixed solution of distilled water to 54.88%, diethylene glycol monobutyl ether (DGBE) to 44.91%, and salt to 0.21%, is filled in a water tank 25, which allows for temperature adjustment. Thereafter, the temperature of the medium is measured using a thermometer 19, a medium characteristic measurement unit 17, and a radiometer 12.

Figure 11:
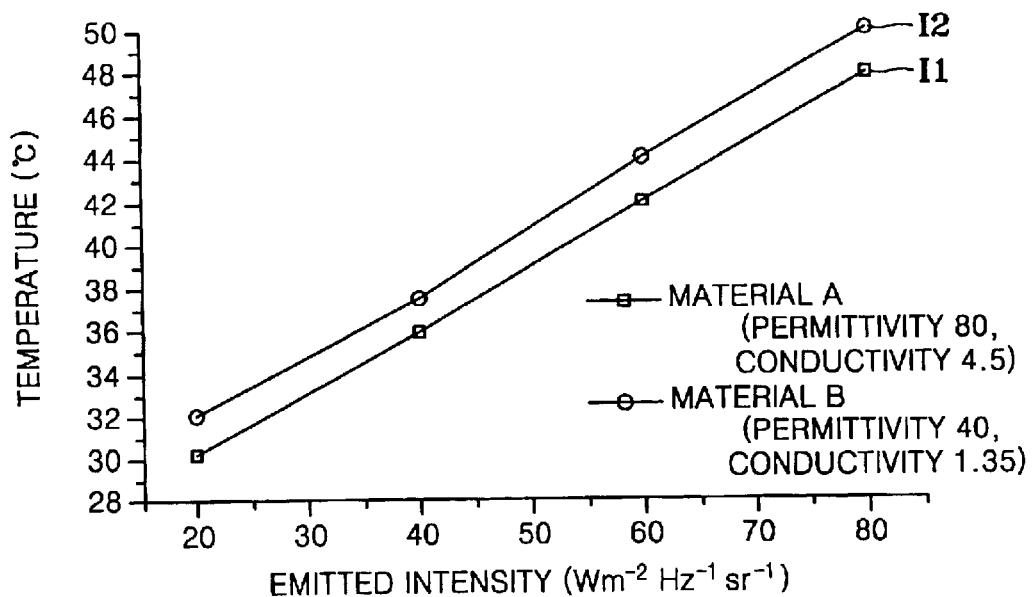
FIG. 11 is a graph illustrating temperature conversion tables of distilled water and mixed solution used in an apparatus for measuring a temperature of a living body according to an embodiment of the present invention.

First, the temperatures of the distilled water as material A having a permittivity of 80 and a conductivity of 4.5, and the mixed solution as material B having a permittivity of 40 and a conductivity of 1.35 are measured using the thermometer 19 and the radiometer 12. Thereafter, a temperature conversion table is established as shown in FIG. 11. Referring to FIG. 11, the graph I1 represents a temperature conversion table of the material A and the graph I2 represents a temperature conversion table of the material B with respect to each emitted intensity (Wm$^{-2}$·Hz$^{-1}$·sr$^{-1}$).

Figure 12:
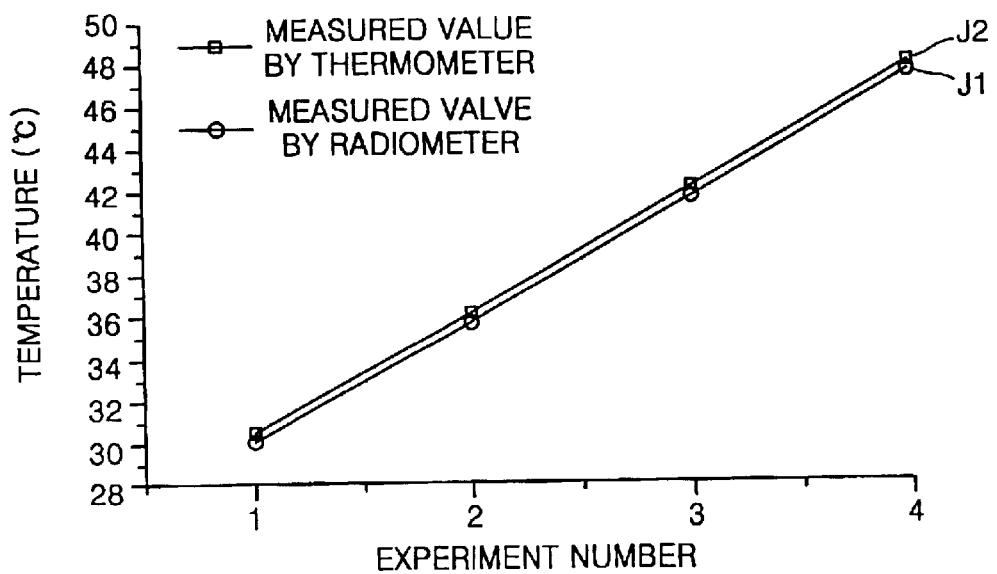
FIG. 12 is a graph illustrating changes in temperatures of distilled water measured by a radiometer and a thermometer using the temperature conversion table of distilled water of FIG. 11.
Figure 13:
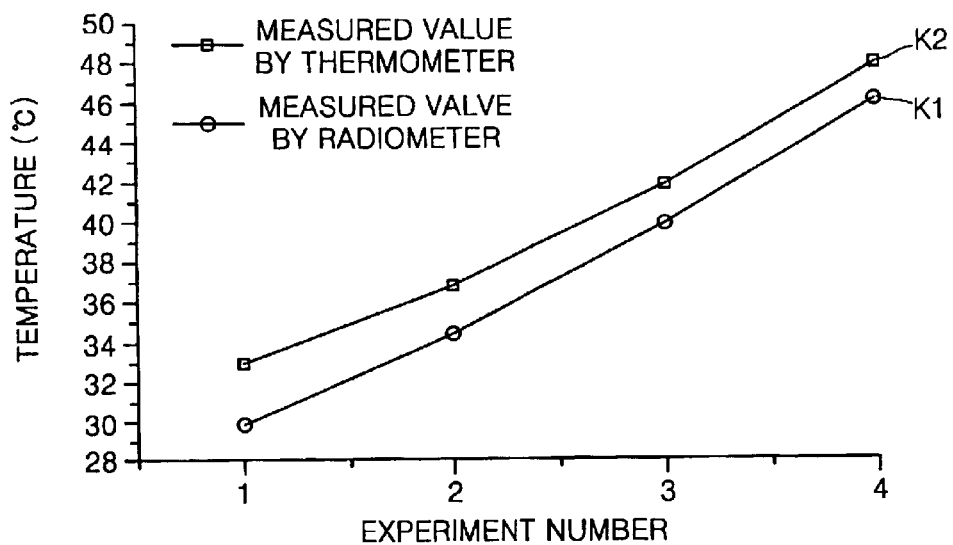
FIG. 13 is a graph illustrating changes in temperatures of a mixed solution measured by a radiometer and a thermometer using the temperature conversion table of distilled water of FIG. 11.
Figure 14:
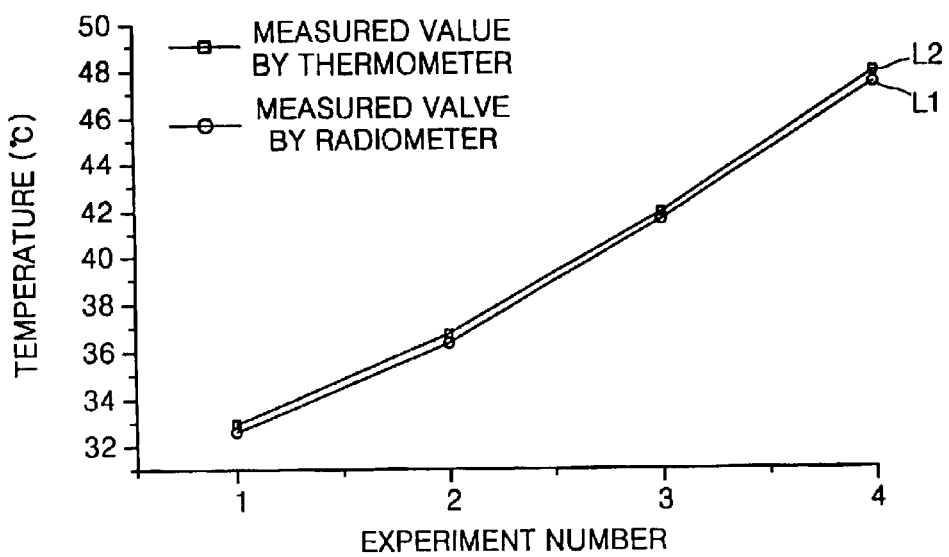
FIG. 14 is a graph illustrating changes in temperatures of mixed solution measured by a radiometer and a thermometer using the temperature conversion table of a mixed solution of FIG. 11.

FIGS. 12 and 13 are graphs illustrating changes in the temperatures of the distilled water and the mixed solution measured by the thermometer 19 and the radiometer 12 using the temperature conversion table I1 of distilled water while varying the temperatures of the distilled water and the mixed solution.

As shown in FIG. 12, when the temperature conversion table I1 of distilled water is used, a measured value J2 by the thermometer and a measured value J1 by the radiometer for the distilled water are almost the same. Accordingly, it is known that reliability of the temperature conversion table I1 of distilled water is high.

However, if the temperature conversion table I1 of distilled water is used for measuring changes in the temperature of the mixed solution, deviations occur between the measured value K2 by the thermometer and the measured value K1 by the radiometer of the mixed solution, as shown in FIG. 13.

When the temperature conversion table I2 of mixed solution is used for the mixed solution, the deviations between the measured value L2 by the thermometer and the measured value L1 by the radiometer are small. Accordingly, it is known that reliability of the temperature conversion table I2 of mixed solution is high.

According to the results shown in FIGS. 10 through 14, the precise temperatures corresponding to the radiation power of the living body may be calculated using the correct temperature conversion table corresponding to the characteristics of the living body.

A method for measuring a temperature of a living body according to an embodiment of the present invention will now be described with reference to FIGS. 15 through 17.

Figure 15:
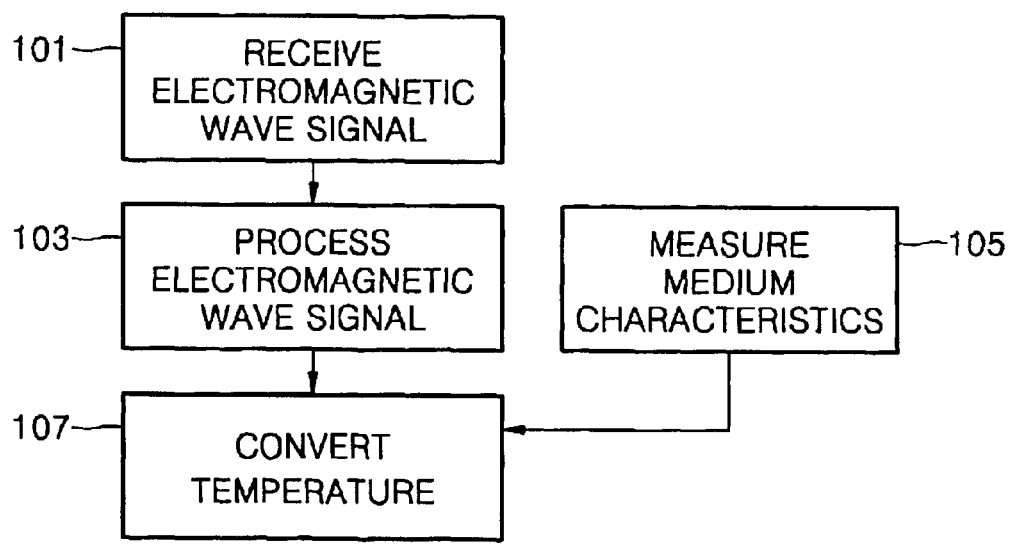
FIG. 15 is a flowchart illustrating a method for measuring a temperature of a living body according to an embodiment of the present invention.
Figure 16:
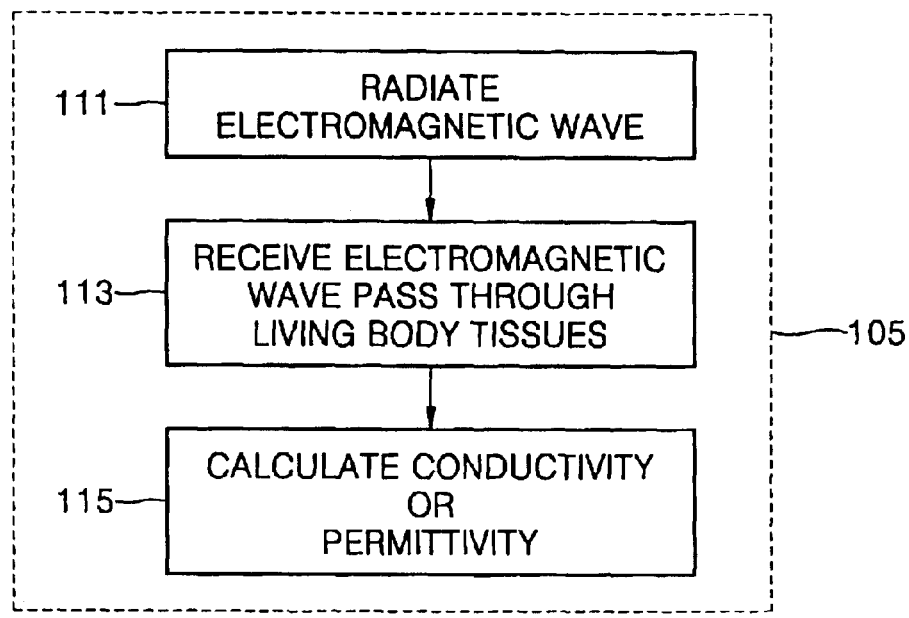
FIG. 16 is a flowchart illustrating a medium characteristic measurement method in the method for measuring a temperature of a living body according to an embodiment of the present invention.

Referring to FIG. 15, in step 101, in order to measure a temperature of a living body, electromagnetic wave signals emitted from a predetermined portion of a living body are received. In step 103, the received electromagnetic wave signals are processed by removing noises, and by filtering and amplifying the received signals. In step 105, the medium characteristics of the living body, such as a conductivity or a permittivity, are measured. Thereafter, in step 107, the output values of steps 103 and 105 are converted into a corresponding temperature.

Referring back to FIG. 16, the process for measuring the medium characteristics of the living body of step 105 may further include, in step 111, radiating electromagnetic wave signals to living body tissues, in step 113, receiving the electromagnetic signals that passed the living body tissues, i.e., transmitting or reflected on the living body tissues, and in step 115, calculating a conductivity or a permittivity using the electromagnetic wave signals.

Figure 17:
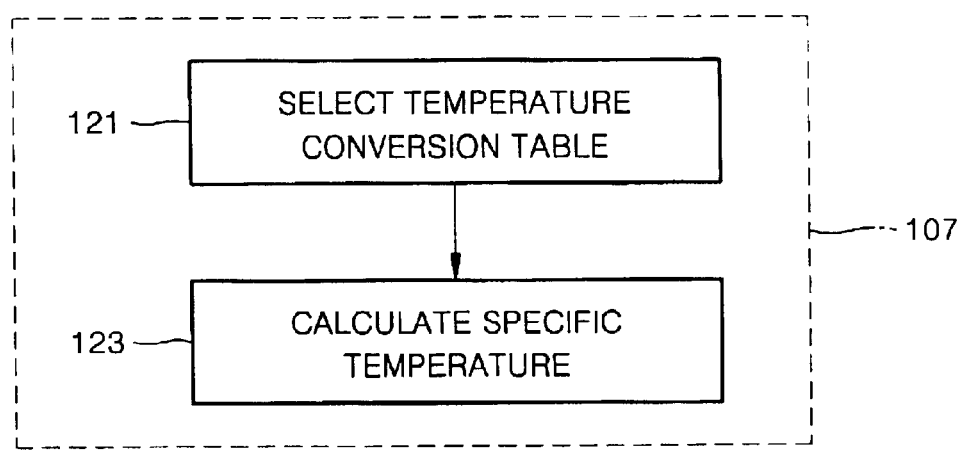
FIG. 17 is a flowchart illustrating a temperature conversion method in the method for measuring a temperature of a living body according to an embodiment of the present invention.

Referring to FIG. 17, the process for converting the temperature of step 107 may further include, in step 121, selecting a temperature conversion table corresponding to the measured medium characteristics, i.e., the conductivity or the permittivity, and in step 123, calculating a specific temperature corresponding to the electromagnetic wave value output in step 103 from the selected temperature conversion table.

The apparatus and the method for measuring a living body temperature according to the present invention provide different temperature conversion tables with reference to radiation power according to the characteristics of a living body medium, i.e., a conductivity and a permittivity, so that reliability of the calculated temperatures is improved.

As described above, the non-invasive apparatus and method for measuring a living body temperature according to the present invention have the advantages of providing temperature conversion tables with respect to radiation power according to the conductivity or the permittivity corresponding to the medium characteristics of a portion of a living body to be measured. Accordingly, precise temperatures for the measured radiation power are provided to improve reliability of the converted temperature and an abnormal state of a human body can be detected and treated at an early stage.

Preferred embodiments of the present invention have been disclosed herein and, although specific terms are employed, they are used and are to be interpreted in a generic and descriptive sense only and not for purpose of limitation. For example, a person skilled in the art may use other characteristics than the conductivity or the permittivity, which are electric characteristics of the medium. Accordingly, it will be understood by those skilled in the art that various changes in form and details may be made without departing from the spirit and scope of the present invention as defined by the appended claims and equivalents thereof.

What is claimed is:

1. An apparatus for measuring a temperature of a portion of a living body, comprising:

a signal receiving unit for receiving electromagnetic wave signals emitted from the portion of a living body to be measured;

a signal processing unit for processing the electromagnetic signals input from the signal receiving unit and outputting a radiation power signal;

a medium characteristic measurement unit for measuring a value of a conductivity or a permittivity of the portion of the living body to be measured and for outputting the measured value; and a temperature conversion unit, including a computer database for storing a plurality of temperature conversion tables with respect to radiation power according to the conductivity or the permittivity of the portion of the living body, for determining a corresponding temperature using the measured value of the conductivity or the permittivity of the portion of the living body and the radiation power signal of the signal processing unit.

2. The apparatus as claimed in claim 1, wherein the signal receiving unit comprises:

a receiver for receiving the electromagnetic signals; and a transmission line for sending the electromagnetic wave signals from the receiver to the signal processing unit.

3. The apparatus as claimed in claim 2, wherein the receiver is an antenna or a probe.

4. The apparatus as claimed in claim 1, wherein the signal processing unit comprises:

an amplifier for amplifying the electromagnetic wave signals input from the signal receiving unit;

a filter for extracting a signal value of a predetermined frequency band from the electromagnetic wave signals;

a noise source for maintaining a reference signal of a specific temperature;

a switch for switching the extracted signal and the reference signal within a specific interval and for connecting to a next stage;

an isolator for processing the extracted signal in one direction and matching circuits; and a detector for detecting an enveloped curve of the extracted signal.

5. The apparatus as claimed in claim 1, wherein the temperature conversion unit comprises:

an information storage unit having a computer database for storing the plurality of temperature conversion tables with respect to radiation power; and an information processing unit for selecting a proper temperature conversion table corresponding to the conductivity or the permittivity measured by the information storage unit and for determining the temperature corresponding to the radiation power signal of the electromagnetic wave input from the signal processing unit, from the temperature conversion tables.

6. The apparatus as claimed in claim 1, wherein the medium characteristic measurement unit comprises:

a signal generator for generating an electromagnetic wave signal of a specific frequency band;

a transmitter for sending the electromagnetic wave signal to the portion of the living body;

a receiver for receiving the electromagnetic wave signal passed through the portion of the living body to be measured;

a signal processor for receiving the electromagnetic wave signal from the receiver and processing the received signal; and a controller for controlling the signal generator and the signal processor.

7. The apparatus as claimed in claim 6, wherein the transmitter and the receiver are integrally formed to receive the electromagnetic wave signals reflected on a predetermined portion of the living body.

8. The apparatus as claimed in claim 6, wherein the receiver receives the electromagnetic wave signal reflected on the portion of the living body to be measured.

9. The apparatus as claimed in claim 1, further comprising a display for displaying the temperature selected by the temperature conversion unit.

10. A method for measuring a temperature of a portion of a living body, comprising:

receiving electromagnetic wave signals from the portion of a living body to be measured;

processing the received electromagnetic wave signals and extracting a radiation power signal therefrom;

measuring medium characteristics, wherein the medium characteristics are conductivity or a permittivity, of the portion of the living body to be measured; and converting a temperature for selecting the temperature of the portion of the living body based on the radiation power signal of the received electromagnetic wave signals and the conductivity or the permittivity of the measuring medium characteristics process.

11. The method as claimed in claim 10, wherein processing the received electromagnetic signals comprises:

removing noise from the electromagnetic wave signals;

extracting the electromagnetic wave signal of a specific frequency band; and amplifying the extracted signal value.

12. The method as claimed in claim 10, wherein measuring medium characteristics comprises:

radiating the electromagnetic wave signal of a specific frequency band to the portion of the living body to be measured;

receiving the electromagnetic wave signal passed through the portion of the living body to be measured; and calculating a conductivity or a permittivity based on the received electromagnetic wave signal.

13. The method as claimed in claim 10, wherein converting a temperature comprises:

selecting a specific temperature conversion table corresponding to the conductivity or the permittivity from a plurality of temperature conversion tables with respect to radiation power, which are previously stored; and calculating a specific temperature corresponding to the radiation power of the electromagnetic wave from the temperature conversion table.

* * * * *